United States Patent [19]
Niemi

[11] Patent Number: 4,548,208
[45] Date of Patent: Oct. 22, 1985

[54] AUTOMATIC ADJUSTING INDUCTION COIL TREATMENT DEVICE

[75] Inventor: Bill H. Niemi, Coon Rapids, Minn.

[73] Assignee: Medtronic, Inc., Minneapolis, Minn.

[21] Appl. No.: 624,871

[22] Filed: Jun. 27, 1984

[51] Int. Cl.⁴ .............................................. A61N 1/40
[52] U.S. Cl. .............................................. 128/419 F
[58] Field of Search ............................... 128/1.5, 419 F

[56] References Cited

U.S. PATENT DOCUMENTS

| | | | |
|---|---|---|---|
| 3,543,762 | 12/1970 | Kendall | 128/422 |
| 4,266,532 | 5/1981 | Ryaby et al. | 128/1.5 |
| 4,428,366 | 1/1984 | Findl et al. | 128/1.5 |

FOREIGN PATENT DOCUMENTS

| | | | |
|---|---|---|---|
| 5713 | 12/1973 | European Pat. Off. | 128/1.5 |
| 143715 | 8/1903 | Fed. Rep. of Germany | 128/1.5 |
| 689156 | 3/1953 | United Kingdom | 128/1.5 |

OTHER PUBLICATIONS

Soloveva et al., "Biomedical Engineering", vol. 7, No. 5, Sep.-Oct. 1973, pp. 291-294.

Primary Examiner—William E. Kamm
Attorney, Agent, or Firm—John L. Rooney; Joseph F. Breimayer; Robert J. Klepinski

[57] ABSTRACT

An apparatus for treating a patient which induces an electric current in the body through external application of an electromagnetic field. The apparatus includes means for controlling the magnitude of the induced electric current by sensing the electromagnetic field and automatically controlling its strength. The sensing may be accomplished through time multiplexed use of the field inducing coil or through the use of a separated, dedicated coil.

9 Claims, 11 Drawing Figures

| Fig.3a | Fig.3b | Fig.3e | Fig.3f |
|--------|--------|--------|--------|
| Fig.3c | Fig.3d | Fig.3g | Fig.3h |

AUTOMATIC ADJUSTING INDUCTION COIL TREATMENT DEVICE

CROSS REFERENCE CO-PENDING APPLICATION

Reference is made to co-pending application Ser. No. 624,872 entitled "AUTOMATIC ADJUSTING INDUCTION COIL TREATMENT DEVICE" by Leonid Shturman and Larry A. McNichols, filed on an even date with this application and assigned to the same assignee.

BACKGROUND OF THE INVENTION

1. Field of the invention

The present invention relates to devices for automatically adjusting stimulating pulses provided to medical treatment induction coils.

2. Prior art

The treatment of the human body by means of magnetic field has enjoyed a long and varied history. One current accepted medical treatment involving induction coils is the assistance in healing of broken bones by the induction of a current across the break through use of a magnetic field passing through the body.

One common configuration for such treatment is to arrange a pair of coils in a Helmholtz relation on opposite sides of the body, so that they are in a flux-aiding relationship. For example, a pair of coils is mounted on a cast on opposite sides of a leg in order to treat a fracture of the tibia.

The size of the coil and the magnitude of the pulsed electrical energy provided to the coils depend upon the size of the bone being treated and the volume of human tissue which surrounds the bone and lies between treatment coils. For example, the coils used in treating a tibia fracture would naturally be larger than those used on the wrist.

In the prior art, the fitting of treatment coils involved custom design of a system for each patient. Coils would be selected and energy provided in a manner which would maximize treatment for the patient. This, of course, is a laborious process which involves initial visits for fitting and later visits for installation of the coils. The physician fitting the coils must take measurements and have a system custom designed.

What is needed in the art is a system which can automatically adjust the electrical energy provided to the coils so that therapy will be maximized.

SUMMARY OF THE INVENION

The present invention involves means for sensing the rate of change of magnetic flux density of a medical treatment coil and automatically adjusting pulses of electrical energy provided to the coil so as to properly provide therapy. In one embodiment, a device includes a medical treatment coil, pulse generator means for producing pulses of electrical energy and supplying them to the coil, a sense coil for sensing the magnetic field produced by the coil, and a controller, responsive to the sensed magnetic field, for automatically generating a signal to the pulse generator circuitry to adjust the magnitude of the pulses.

In another embodiment, the device includes first and second treatment coils and a multiplexer electrically connected to the coils for selecting either or both of the coils. One of the coils is activated by electrical pulses from a pulse generator. A controller, electrically connected to the multiplexer, selects the other coil for sensing the strength of the magnetic field (dB/dt) produced by the first coil and for, based upon the sensed magnitude, sending a signal to the pulse generator means indicating the magnitude of electrical pulses to be provided to the first coil.

DETAILED DESCRIPTION OF THE PREFERRED EMBODIMENTS

Figure 1:
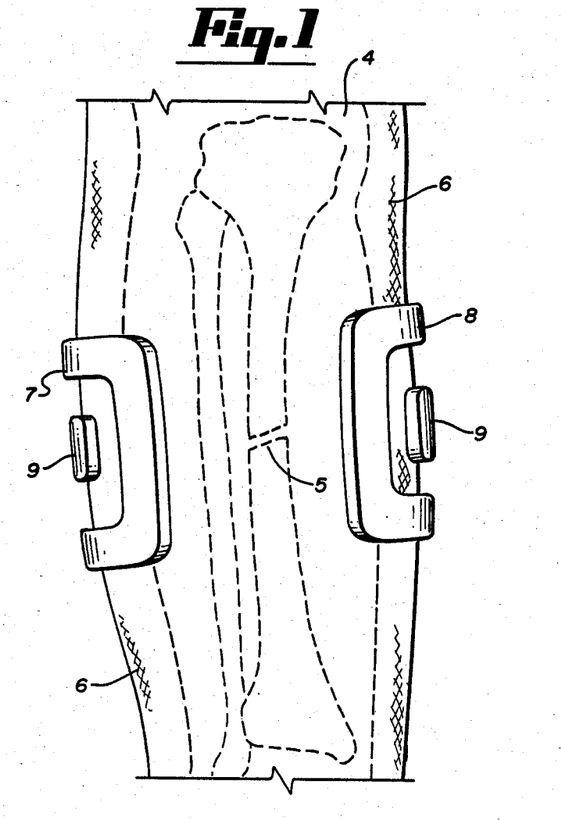
FIG. 1 is a fragmentary, partially cut-away, view of the leg of a human patient with first and second treatment coils mounted on a cast and feedback coils mounted within the treatment coils.

An example of a treatment method using induction coils is illustrated in FIG. 1 where a leg 4 includes a bone 5 with a fracture. A cast 6 is mounted on leg 4 to immobilize it. Treatment coils 7 and 8 are mounted on opposite sides of leg 4 in a flux-aiding relationship so that a magnetic field extends through the center of both coils 7 and 8. Feedback coils 9 are small coils mounted on cast 6 within the center of coils 7 and 8.

Feedback coils 9 are illustrative of one embodiment of the present invention. Feedback coils 9 are used in this embodiment to sense the magnetic field produced by coils 7 and 8. In the preferred embodiment primarily described herein, separate feedbacks coils 9 are not used. Instead, performance of coils 7 and 8 is checked by alternatively using one coil as a treatment coil and the other coil as a sense coil.

Figure 2:
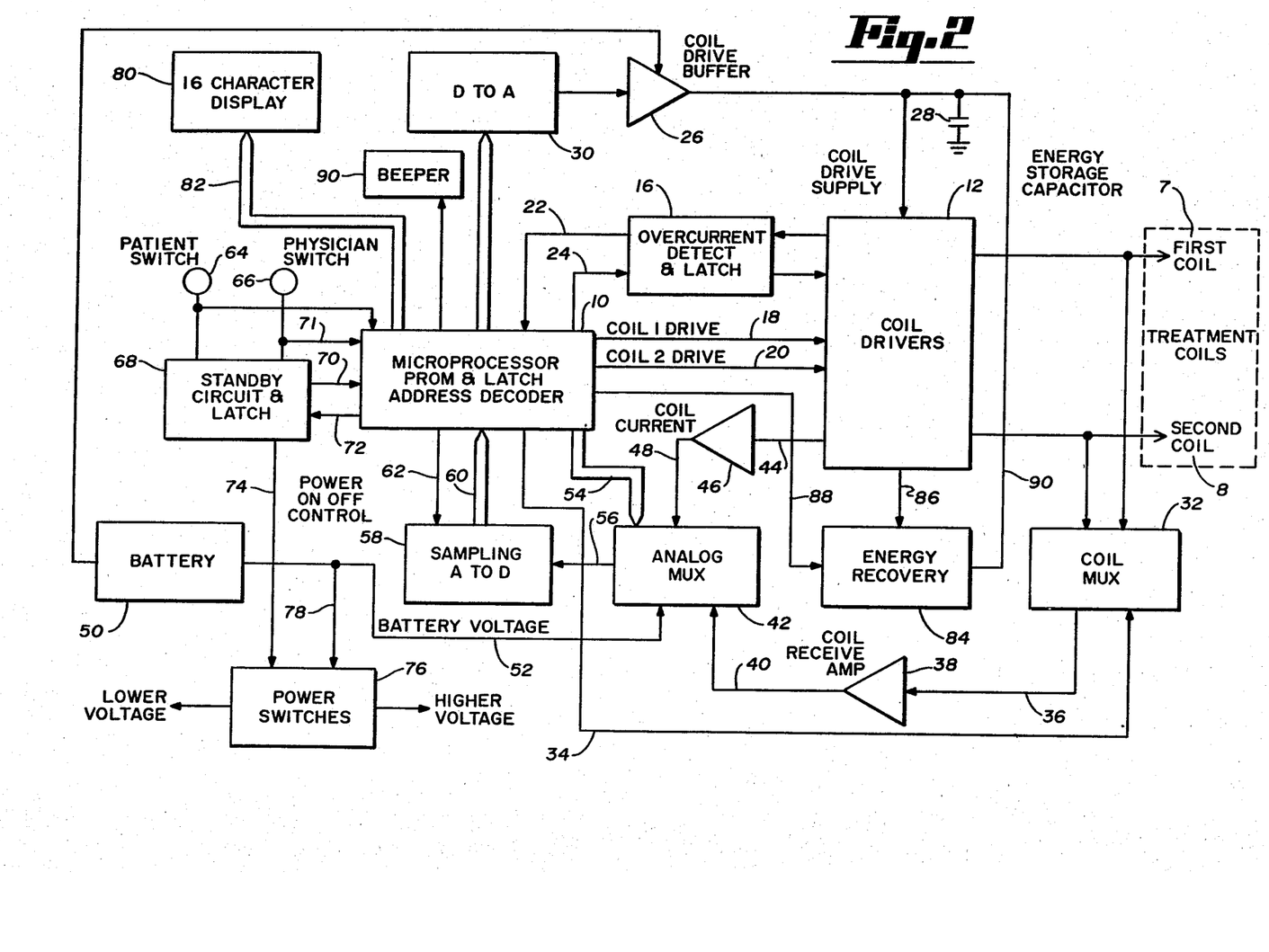
FIG. 2 is a block diagram of a medical treatment device including automatic adjusting means of the present invention.

The block diagram of FIG. 2 illustrates the preferred embodiment in which coils 7 and 8 may each be used to sense performance of the other. This embodiment is centered around a microprocessor 10 which includes a PROM, a latch and an address decoder.

A pair of coil drivers 12 provides pulses of electrical energy to treatment coils 7 and 8. An overcurrent detection and latch circuit 16 senses when pulses provided by coil driver circuitry 12 exceeds a specified maximum peak current.

Microprocessor 10 communicates through first coil drive line 18 and second coil drive line 20 with coil driver circuitry 12. Should overcurrent detect and latch circuit 16 detect a threshold value put out by coil driver circuitry 12, it communicates with microprocessor 10 through line 22, indicating that the system is in overcurrent mode. Microprocessor 10 uses line 24 to clear the latch of overcurrent detect and latch circuitry 16. Such an overcurrent could be caused by such things as a short in a coil, a faulty coil, or a faulty cable.

The power to be used by coil driver circuitry 12 for producing pulses of electrical energy is supplied by coil drive buffer 26 and energy storage capacitor 28. This process also involves digital to analog converter 30. Microprocessor 10 provides a digital signal indicative of desired pulse amplitude to digital to analog converter 30. From this, digital to analog converter 30 creates an analog signal to be used by coil drive buffer circuitry 26. Coil drive buffer circuitry 26 provides regulated battery power to charge capacitor 28 to a controlled voltage.

The digital signal from microprocessor 10 to digital analog circuitry 30 is provided once for each time the unit is turned on. This value is stored in the latch of the digital to analog converter 30.

Capacitor 28 attempts to recharge continuously. Coil drive buffer circuitry 26 acts in a manner similar to a voltage regulator that attempts to regulate energy storage capacitor 28 to a voltage determined by the analog output of digital analog converter 30. As a pulse from coil drive circuitry 12 lowers the charge on energy storage capacitor 28, the charging process starts again.

Coils 7 and 8 are connected to coil multiplexer 32 which can select either coil for monitoring. Coil multiplexer 32 receives communication signals on line 34 from microprocessor 10. Microprocessor 10 signals along line 34 which coils to be selected by coil multiplexer 32. For example, microprocessor 10 drives first coil 7 through means of line 18 and coil driver 12 while indicating along line 34 that second coil 8 is to be sensed via coil multiplexer 32.

The output of coil multiplexer 32 is connected along line 36 to a coil receive amplifier 38. Amplifier 38 is a differential amplifier which amplifies a signal on line 36 and puts out an amplified signal on line 40.

The amplified signal on line 40 is provided to an analog multiplexer 42. Multiplexer 42 is used to select various forms of analog input to be interpreted by a microprocessor 10.

Coil current from coil driver circuitry 12 is sensed on line 44 and provided to a coil current amplifier 46 which amplifies the signal and provides an amplified signal on line 48 to analog multiplexer 42. The coil current signal on line 44 comes through a current sensing resistor that is part of coil driver circuitry 12. In this manner, total current through coils 7 and 8 is tested.

An additional input to analog multiplexer 42 is voltage from battery 50 which is provided on line 52. Battery 50 is also directly connected to coil drive buffer circuitry 26.

Therefore, analog multiplexer 42 provides a choice of three analog inputs: battery voltage from battery 50, coil voltage on line 40 from coil receive amplifier 38, and coil current on line 48 from coil current amplifier 46. Microprocessor 10 provides digital signals on line 54 to indicate to analog mux 42 which of these three inputs to select.

Whichever of the three analog inputs is selected in analog mux 42 is provided as output on line 56 to a sampling analog to digital converter 58. Analog to digital converter 58 converts the signal on line 56 to a digital signal for use by microprocessor 10. The digital signal is provided on line 60. A line 62 from microprocessor 10 instructs analog to digital converter 60 when to convert data. Analog to digital 60 converter is a sampling type of device which requires a signal during a certain sampling window as determined by microprocessor 10. Therefore, voltage pulses are sampled at chosen points and times during pulse duration.

There are various system functions that can be tested by the three forms of input to analog multiplexer 42. The voltage read from coils via coil multiplexer 32 is needed to determine at self-fitting time how far apart coils 7 and 8 are. It is also used to decide how to set the drive pulses through coil drive supply circuit 12 such that the dB/dt or the rate of change of flux midway between treatment coils 7 and 8 is at the prescribed level.

The coil current monitored on line 44 is used to tell which of two or more different types of coils is in use. This is commonly done upon the start up of the system at self-fitting time. Different coils are of different inductance. By monitoring the current towards the end of a treatment pulse, it determines which type of coil is in use. Additionally, ths current is used to determine if the system is working properly. If there is a failure in one coil it could be recognized by sudden drop in current or, in some cases, by an increase in current in that coil.

Battery voltage is sensed along line 52 to know when to charge the battery. It also indicates that there is battery failure. This type of system preferably uses rechargeable batteries. If the batteries are being charged and the battery voltage doesn't increase after a period of time, it is known that there is a battery failure.

The system is activated by patient switch 64 or physician switch 66 which are both connected to microprocessor 10 and standby circuit and latch 68. Patient switch 64 acts generally as an on/off switch. Microprocessor 10 is maintained in a standby mode and is activated when patient switch 64 is depressed. The standby mode maintains the volatile memory in RAM. When patient switch 64 is initially pushed, it causes standby circuit and latch 68 to clear a standby flip-flop putting the system out of standby mode. Standby circuit and latch 68 alerts microprocessor 10 via line number 70 that it is time for microprocessor 10 to come out of standby mode.

If the patient switch 64 is activated a second time, it instructs the microprocessor 10 that its time to go back into standby. Microprocessor 10 then signals, via line 72, for the standby circuit and latch 68 to go back to standby.

Additionally, if battery voltage drops too low, the system goes into a standby state. In this embodiment, if the battery voltage drops below 10 volts, microprocessor 10 turns the system to standby.

Standby circuit and latch 68 is connected by line 74 to power switches 76. Battery 50 is connected to power switches 76 by line 78. Power switches 76 regulate power to most of the circuitry of the unit. There are 5 volt and 12 volt switches to provide appropriate voltage to various parts of the circuit. Most of the circuitry will be shut off through power switches 76 during standby mode. There are only a few components that are kept alive during standby, such as microprocessor 10.

Power switches 76 include a 5 volt regulator that steps the battery voltage down from about the nominal 12 volts to the 5 volt switched level.

Physician switch 66 can also take the system out of standby, clearing the standby latch. Physician switch 66 is used to indicate to microprocessor 10, via line 71, what mode the system is to be in. The physician initiates self-fitting mode by depressing physician switch 66, in this embodiment for a period of eight seconds. Also, various system messages are inspected by momentarily depressing physician switch 66.

A 16 character LCD display 80 is connected to microprocessor 10 by line 82. Display 80 is used to display messages during operation of the unit, including error messages.

An energy recovery circuit 84 receives electrical energy on line 86 from coil driver circuitry 12 as treatment coils 7 and 8 discharge. Energy recovery circuit 84 sends energy back along line 90 to energy storage capacitor 28, for use in the next drive cycle. Energy recovery circuit 84 receives information from microprocessor 10 along line 88.

A beeper 90 is connected to receive signals from microprocessor 10. Beeper 90 is used for giving audible signal of things such as low battery warnings.

CIRCUIT DESCRIPTION

Figure 3:
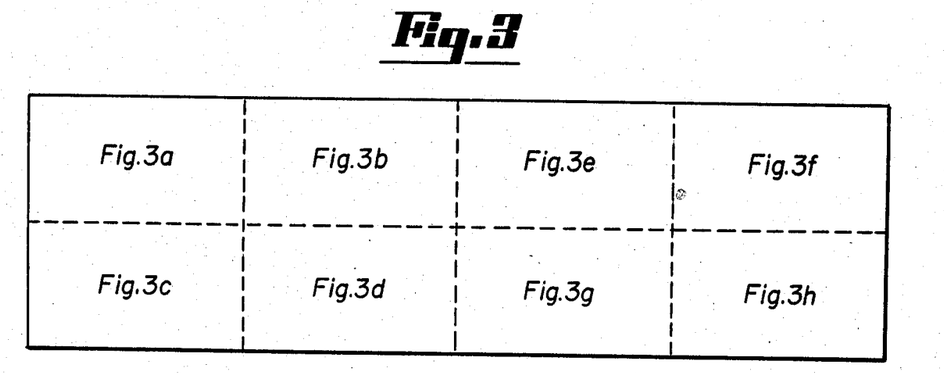
FIG. 3 is a layout of FIGS. 3a-3h, which are electrical schematics of the device of FIG. 2.

Microprocessor 10 includes microprocessor U11 which is a HD6303B processor manufactured by Hitachi. This is an eight-bit CMOS low-power microprocessor. Microprocessor 10 also includes latch U12, PROM U14, address decoder U13, as well as gating control logic consisting of U9B, U9C, and U9D. Latch U12 separates address information from data information. The PROM U14 address lines A0 through A7 require address information. Microprocessor U11 puts out both address and date information from pins 30-39 which are labeled $A_0/D_0$-$A_7/D_7$. At various points in the timing cycle, information coming out on the combined address and data bus is either address information or data information. Latch U12 latches in address information during appropriate timing, as controlled by the latch enable input of latch U12 (pin 11) which is connected to the address strobe output on microprocessor U11 (pin 39). Latch U12 is a 74HC373 device which is manufactured by various companies.

PROM U14 stores a sequence of instructions used in controlling the system. PROM U14 is standard programmable read only memory which is eraseable by ultraviolet light. Address information comes to the microprocessor U11 through address latch U12 and indicates the program step. The lower eight bits of address come via this latch. The upper five bits of address information come directly off the upper address bus which is only an address bus and not a combined address and data bus. This is on ports A8 through $A_{13}$.

Clock enable input on PROM U14 comes through the address decoder U13. Address decoder U13 is set up to decode an address of EXXX through FXXX. Any address in this range would enable PROM U14.

Data lines $D_0$-$D_7$ from PROM U14 have eight bits of data information and are connected directly to the combined address and data bus of microprocessor U11.

Microprocessor U11 controls timing functions, keeps track of treatment time, counts the number of treatment sessions, monitors error conditions, displays appropriate messages, and indicates errors in functioning of the system.

The microprocessor U11 is connected to display 80 through the address bus. For timing purposes, information sent to the display is sent as address information.

Microprocessor 11 is the location in the circuit through which all information flows. Lines 18 and 20 for coil 7 and coil 8 are connected to ports 12 and 13 respectively of microprocessor 11. In this embodiment, the digital components are primarily mounted on one board and analog components on another. Line 18 comes in from a board-to-board connector. It is connected to voltage translator U3. Line 18 enters U3 as a 0-5 volt logic level signal. This is also true of line 20, for coil 8. Voltage translator U3 converts the 0-5 volt level to a 0-9 volt level. Pin number 3 of voltage translator U3 is connected to resistor R11 and pin 6 is connected to resistor R12, both of which are connected to ground. Resistors R11 and R12 are pull down resistors to force pins 3 and 6 to a known state when power is switched off. Voltage $V_{cs}$ is connected to pin 1 of voltage translator U3. During standby condition $V_{cs}$ is removed. Pin 8 is the ground for voltage translator U3. Pins 15 and 9 are connected to ground to disable section C and D of voltage translator U3 which are not used. Only sections A and B are used. Output on pins 4 and 5 is stepped up. Ports E and F of voltage translator U3 are the output locations for the translated voltage.

This output goes to buffers made up of U2A through U2D. Coil 7 and coil 8 are identically treated internally so only one path will be described, for sake of the simplicity of the description. The first coil 7 path goes to a buffer made up of amplifiers U2A and U2B connected in parallel, which provide additional current drive. These are noninverting buffers. The low drive impedance from this buffer is needed to drive the gate of FET Q3 in order to increase the switching speed. The gate has significant capacitance associated with it, so a low drive impedance is needed to switch the capacitance in a short time. The gate is also connected through pull down resistor R7 to ground, to be sure that the gate is pulled to ground during standby when FET Q3 is to remain off.

The source of FET Q3, as well as FET Q4 from the other path, is connected to resistor R9. Resistor R9 is part of the current sensing circuit. Resistor R9 is a four leaded 0.01 ohm resistor. There are four leads so that there are two leads for the high current path and two leads for sensing. The high current path is the source of FET Q3 and FET Q4 on one side. The other side is connected to the negative side of capacitor C2 which in turn goes to analog ground. High currents go through this path. These currents can be up to 10 or 11 amps peak. The other two leads of resistor R9 have a low current path which is connected to current amplifier U1B and U1C. One lead is connected through resistor R41 to the inverting input of U1B, and the other low current lead is connected through resistor R20 to the non-inverting input of U1B. Amplifier U1B is connected in a differential amplifier scheme. The output of differential amplifier U1B goes to the noninverting input of amplifier U1C. The inverting input is connected both to ground through resistor R18 and through R17 to provide feedback. Amplifier U1C is a single-ended input amplifier which provides additional gain from amplifier U1B. Output of amplifier U1C goes to a multiplexer U6.

The drain of FET Q3 is connected to one side of treatment coil L2 and the drain of power FET Q4 is connected to one side of coil L1.

Coil drive buffer 26 includes transistors Q1 and Q2, amplifier U1A, and resistors R1-R5 and R12. A terminal of coil L1 and coil L2 is each connected to a common connection at the drain of transistor Q1, which is a series pass P-channel power FET transistor. The gate of transistor Q1 is connected through transistor Q2 and resistor R2. Base of transistor Q2 is connected through resistor R5, which is the output of amplifier U1A, which gets its reference input on the noninverting input pin 3 from digital to analog inverter 30 output. This is a signal from 0 to 2½ volts. The digital to analog converter 30 is carrying the signal from microprocessor 11 indicating amplitude. This 0 to 2.5 volt signal comes to the noninverting input of amplifier U1A. The inverting input of amplifier U1A is connected to ground through resistor R12. The inverting input is also connected through resistor R4 and R3 back to the coil drive supply off the drain of transistor Q1. R4 and R3 provide the feedback path. Resistor R3 allows fine adjustment of the coil drive amplitude for calibration.

Transistor Q2 provides one additional inversion. Transistor Q2 acts together with amplifier U1 to provide gain. Transistor Q2 is driven into conduction and the more transistor Q2 conducts, the more the gate of transistor Q1 is driven to a low state. This causes increased voltage from source to gate of transistor Q1. Because it is a P-channel enhancement mode power FET, the higher the source to gate voltage, the more transistor Q1 will be driven into conduction. Batteries are connected to the gate via pull up resistor R1. Therefore the amount of voltage from source to gate of transistor Q1 determines the power that is provided to the coils L1 and L2. Buffer 26 is configured in a feedback circuit to maintain voltage across capacitor C2, which is connected across from the common coil drive to analog ground. The voltage across C2 is to be maintained a constant level determined by the digital to analog output as controlled by microprocessor 10.

The circuit has provision for connecting a battery charger to charge battery 50. The charger can be connected to the unit while the unit is providing treatment output so battery 50 can be charging at the same time the current is supplied to the circuit. Diode CR1 prevents current from flowing into the charger from battery 50 in the event that the charger should fail or output pins of the charger should short out. The positive side of the battery 50 is connected through fuse F1 as a safety feature to prevent overheating in the event that there is a short in the system.

Coil current amplifier 46 includes amplifiers U1B and U1C, resistors R17, R18, R19, R20, R21 and R41. U1B is configured as a simple differential amplifier amplifying the differential voltage across the two sensing leads of current sensing resistor R9. One sensing lead is connected to the inverting input of U1B through resistor R41 and another sensing lead is connected to the noninverting input of U1B through resistor R20. Resistor R21 completes a divider network with resistor R20. Resistor R19 provides feedback from the output of U1B to the inverting input of U1B. The output of U1B is further amplified by noninverting amplifier U1C, whose gain is controlled by resistor divider network formed by resistors R17 and R18. The output of U1C is connected via line 48 to the analog multiplexer.

Overcurrent detect and latch circuit 16 includes amplifier U1D, resistors R13 through R16, capacitor C3 and C4, and NAND gates U8B and U8C.

Amplifier U1D is configured as a comparator. At amplifier U1D, the circuit uses current sensing resistor R9 connected through resistor R57, which goes to the inverting input of U1D. The noninverting input of amplifier U1D is maintained at a fraction of fixed reference voltage $V_{Ref}$. Voltage $V_{Ref}$ is divided down by a voltage divider network consisting of resistors R13 and R16. Capacitor C4 provides filtering to minimize noise on the noninverting input. Amplifier U1B is configured as a comparator. The amplifier circuit is configured so the output of amplifier U1D will either be in a high state or a low state. Resistor R14 pulls that output to ground when $V_{ds}$ is switched off. When $V_{ds}$ is on, the comparator is allowed to function normally. When the inverting input amplitude on pin 13 exceeds the noninverting input reference on pin 12, the output of comparator on pin 14 goes to ground or very near ground which puts out a signal at zero logic level. When this line goes low, a latch consisting NAND gates U8B and U8C will be set. NAND gates U8B and U8C are configured in a set/reset latch configuration. An output of that set/reset latch goes to microprocessor U11. When output on pin 10 is in the low state, it indicates to the microprocessor on port 11 (pin 14) that the system is in an overcurrent state. Microprocessor 11 then, through software takes appropriate action. Another line coming from microprocessor port 10 clears the overcurrent latch when pulsed low by microprocessor 11.

The overcurrent detect and latch circuit 16 disables coil drivers 12 by the enable input on pins 2 and 7 of voltage translator U3. When this pin is low, indicating overcurrent conditions, U3 outputs will be disabled, shutting off coil drivers 12. This overcurrent disable is a fast acting pathway that does not go through microprocessor 11 so that coil driver circuitry 12 will be shut down immediately upon overcurrent condition.

Coil multiplexer 32 includes section C of multiplexer U6. Multiplexer U6 has three different sections used in different portions of this circuitry. Section C includes pins 3, 4, 5 and 9. Pin 3 (CY) and pin 5 (CX) are connected to coils L1 and L2 via resistors R22 and R52. The control for this section of multiplexer U6 comes from pin 9 (C). Input to pin 9 comes through a voltage level translator U5 which is connected to microprocessor 11. When pin 9 is low, pin 5 (CX) is connected to the common input pin 4. When pin 9 is high, then pin 3 (CY) is connected to common pin 4.

Figure 3A:
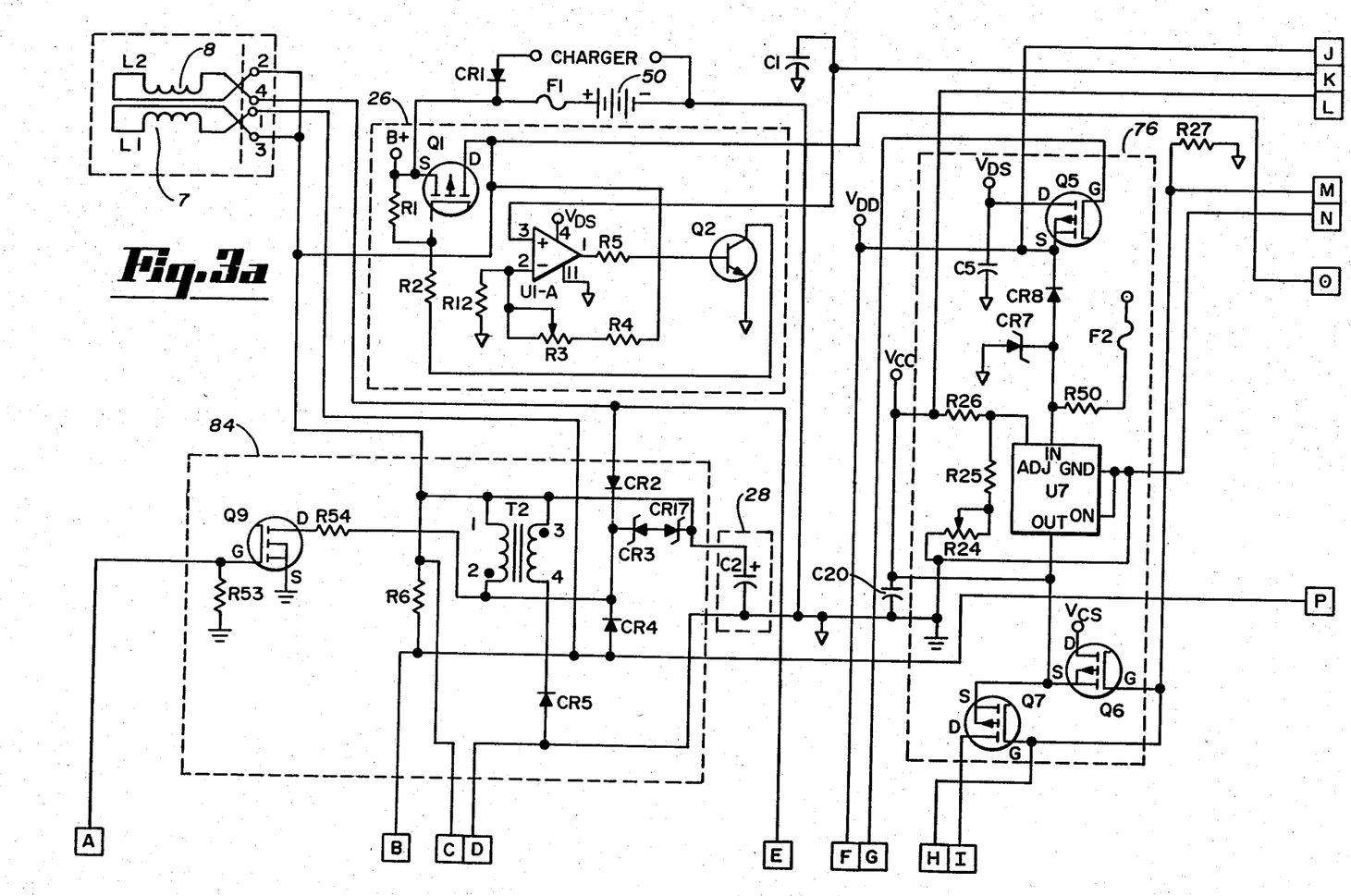
Figure 3B:
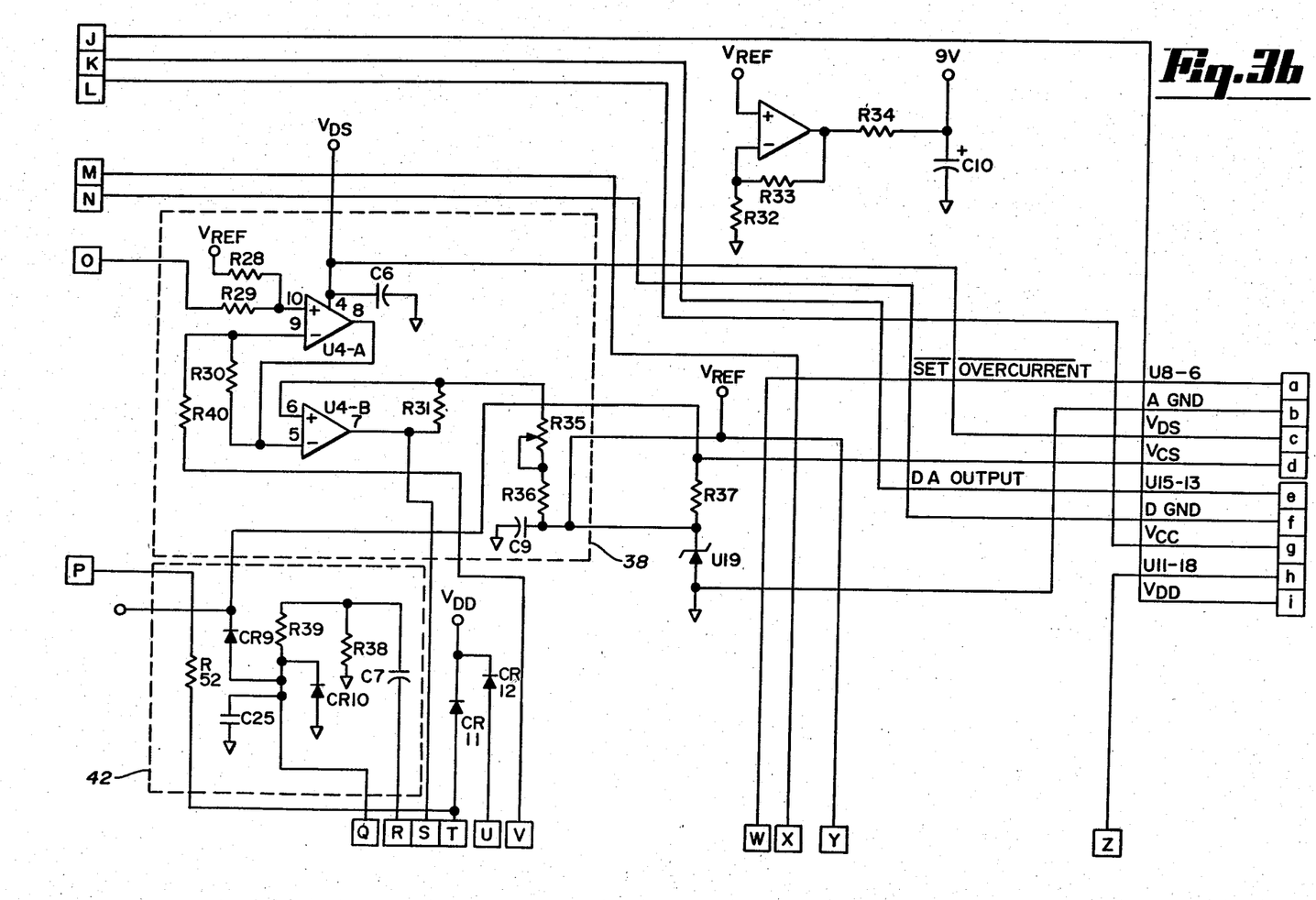
Figure 3C:
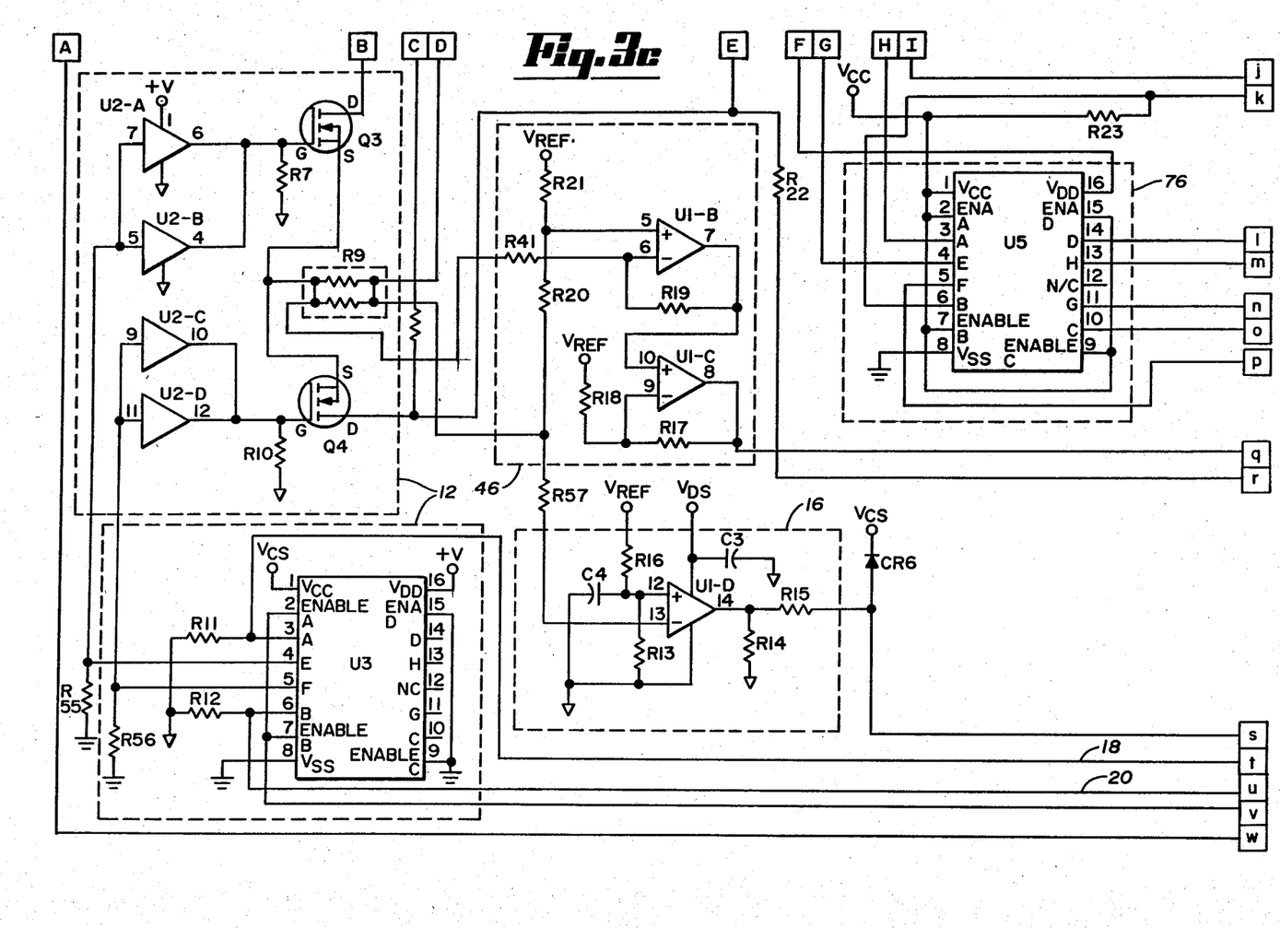
Figure 3D:
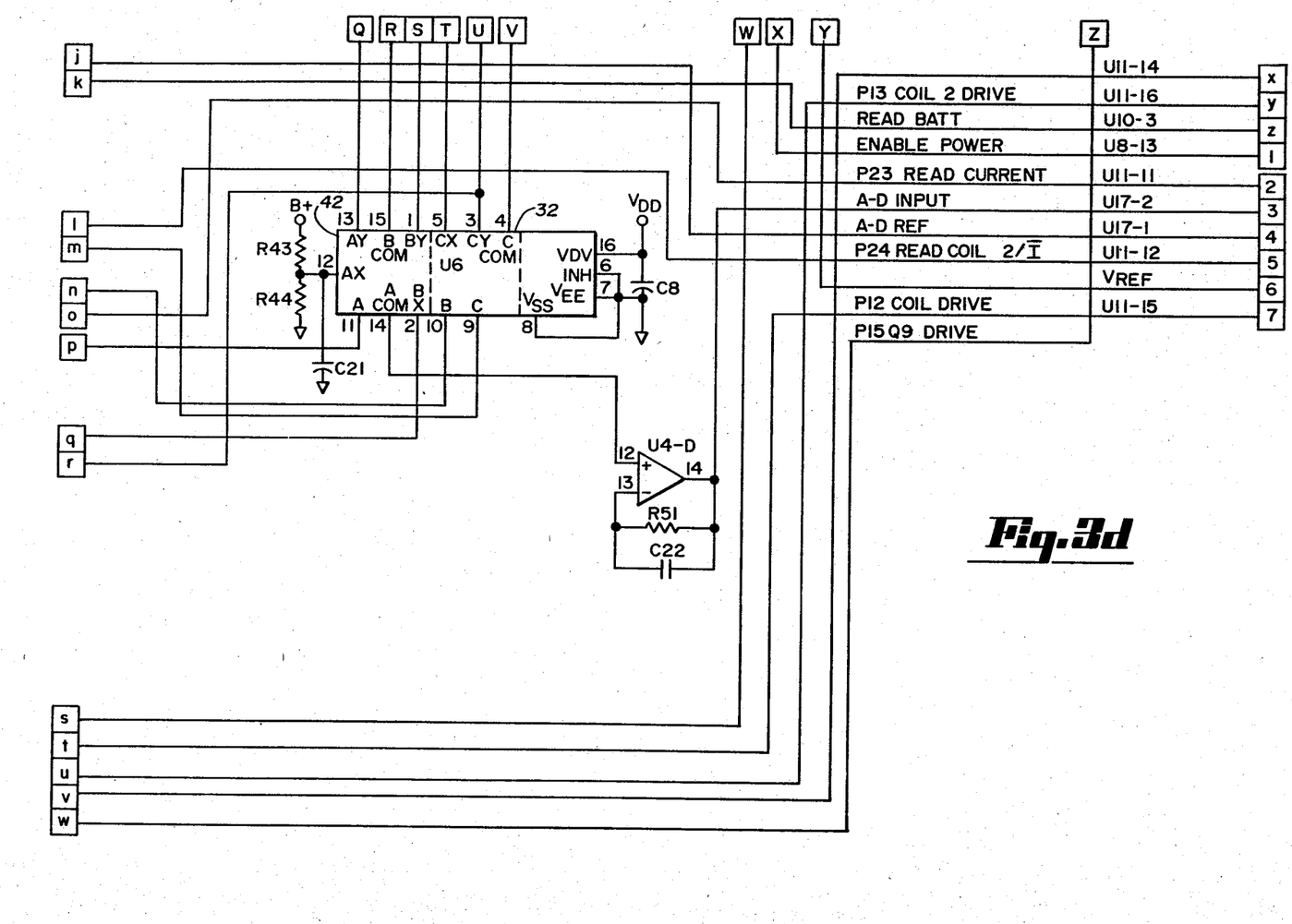

The output of multiplexer 32 (FIG. 3d) is common pin 4 (C) to coil receiving amplifier 38 (FIG. 3b). In coil receiving amplifier 38, this input goes through resistor R40 to differential coil amplifier U4A at the inverting input. The noninverting input of amplifier U4 is connected through resistors R29 back to the common side of the coils. Amplifier U4A is configured in a linear differential amplifier configuration and its output is an analog voltage proportional to the differential voltage across the receiving coil. The output of amplifier U4A goes to the noninverting input of amplifier U4B. The inverting input of amplifier U4A is tied to resistor 30 and to the noninverting input of U4B. Resistor R30 is a feedback resistor from the output of amplifier U4A pin 8 to the inverting input pin 9, which is part of the differential amplifier configuration. The inverting input of amplifier U4B goes through feedback resistor R31 from the output of amplifier U4B. Amplifier U4B provides additional gain off the first stage of amplification from amplifier U4A. Two stages of amplification are used to provide the required band width and gain needed to effectively reproduce the voltage waveform that is being monitored.

The output of amplifier U4B goes into multiplexer 42 which is another section of multiplexer U6. It enters pin 1 (BY) of multiplexer U6 which comprises analog multiplexer 42. From there the signal goes to the pin 15 (BCOM), when multiplexer 42 is in the proper position, as controlled by input pin 10 (B) which ultimately comes from microprocessor 11. When input at pin 10 is in the high state, pin 1 (BY) will be connected to pin 15 (BCOM). The output BCOM goes through a filter network consisting of a capacitors C7 and C25, resistors R38 and R39 and clamping diodes CR9 and CR10. The signal eventually arrives at another section of the multiplexer which is pin 13 (AY). Pin 13 (AY) will be connected to pin 14 (ACOM) when the controlling input at pin 11 (A) is at a logical 1. This control comes from microprocessor 11. Output from pin 14 (ACOM) is buffered by amplifier U4D which is a unity gain amplifier. This amplifier provides low impedance drive to the input of analog to digital converter 58. Section C of multiplexer U6 is used to choose one of two coils for a voltage readback. Section B either selects voltage input from coil amplifier U4B or selects input BX from the current amplifier. When control input B at pin 10 of multiplexer U6 is at a 0 level, BX will then be connected to BCOM. The signal from BCOM output will now go through the same input filter network as mentioned previously. The signal is then ultimately connected to the analog to digital converter 58.

A line from battery 50 for sensing battery voltage comes through the resistor divider network consisting of resistors R43 and R44. Analog to digital converter 58 only accepts voltages up to 5 volts, so battery voltage is divided down before being supplied to converter 58. Divided down battery voltage is selected when input AX is connected to ACOM. This occurs when pin 11 (A) is set at logic 0. When pin 11 (A) is at a logic 1, the AY is connected to read current or voltages. Sampling analog to digital converter 58 includes converter U17. A signal from multiplexer 42 arrives on pin 2 of converter U7 which is called $V_{IN}$. Reference input on pin 1 comes from a 5 volt supply line. Capacitor C24 is connected from pin 1 to ground. Capacitor C24 provides filtering on the reference input to minimize noise and ripple on the line to provide a stable reference input. Frequency divider U16 provides a clock signal. Frequency divider U16 is a 2:1 frequency divider. The base frequency is supplied on pin 3 of divider U16 which comes from enable input pin 40 of microprocessor 11. The basic bus system clock runs at 500 kilohertz. Divider U16 divides this down to a suitable frequency for converter U17.

Sampling A to D converter U17 (FIG. 3g) is initiated by pulling the write pin 15 low in conjunction with forcing the pin 16 chip select line low. Pins 15 and 16 are controlled by microprocessor 11. Select pin 16 is brought low whenever any address in the range CXXX-DXXX is decoded by address decoder U13. Connections from the microprocessor 11 to converter U17 are on the common data bus. This connection is on bus lines $D_0$-$D_7$.

Figure 3E:
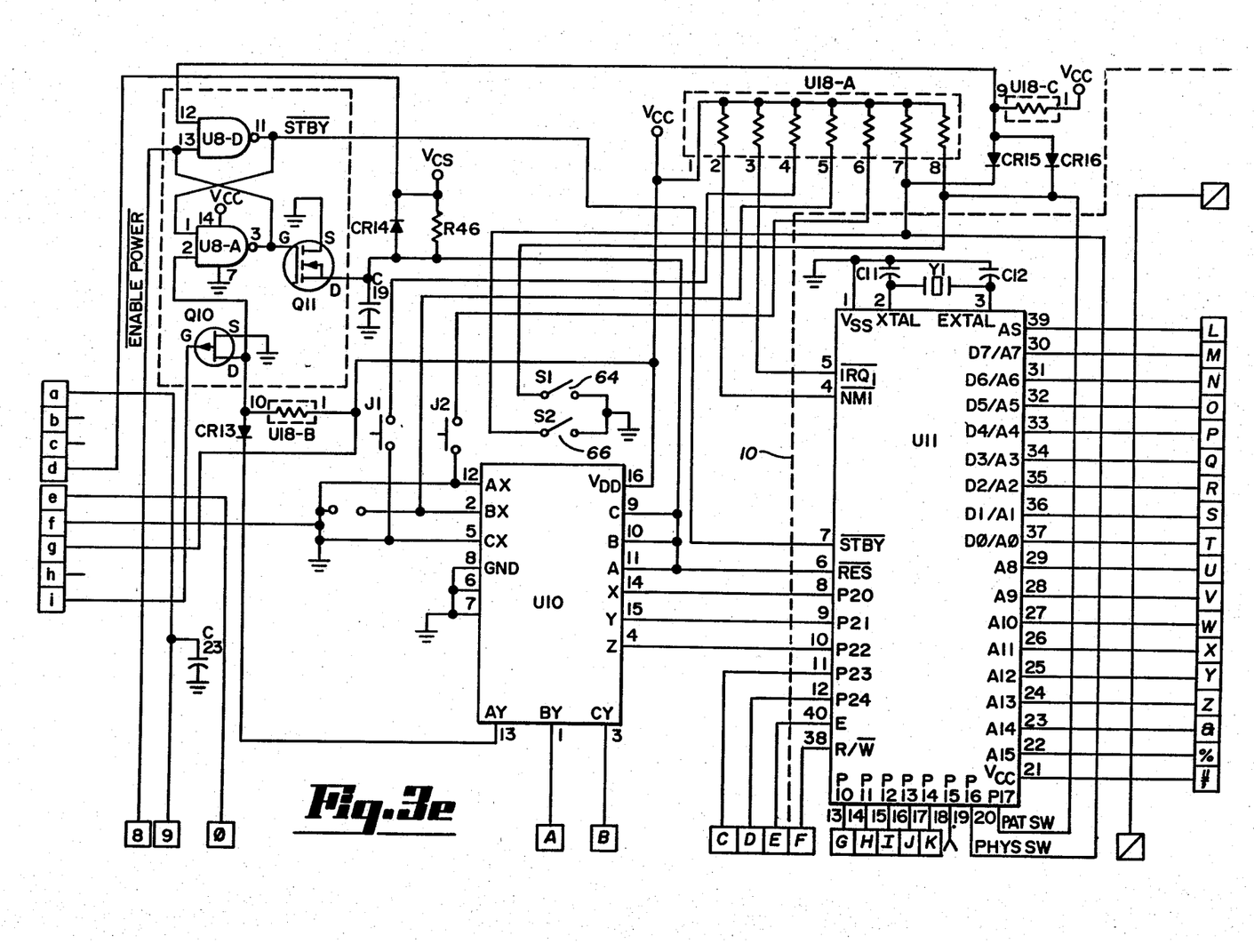
Figure 3G:
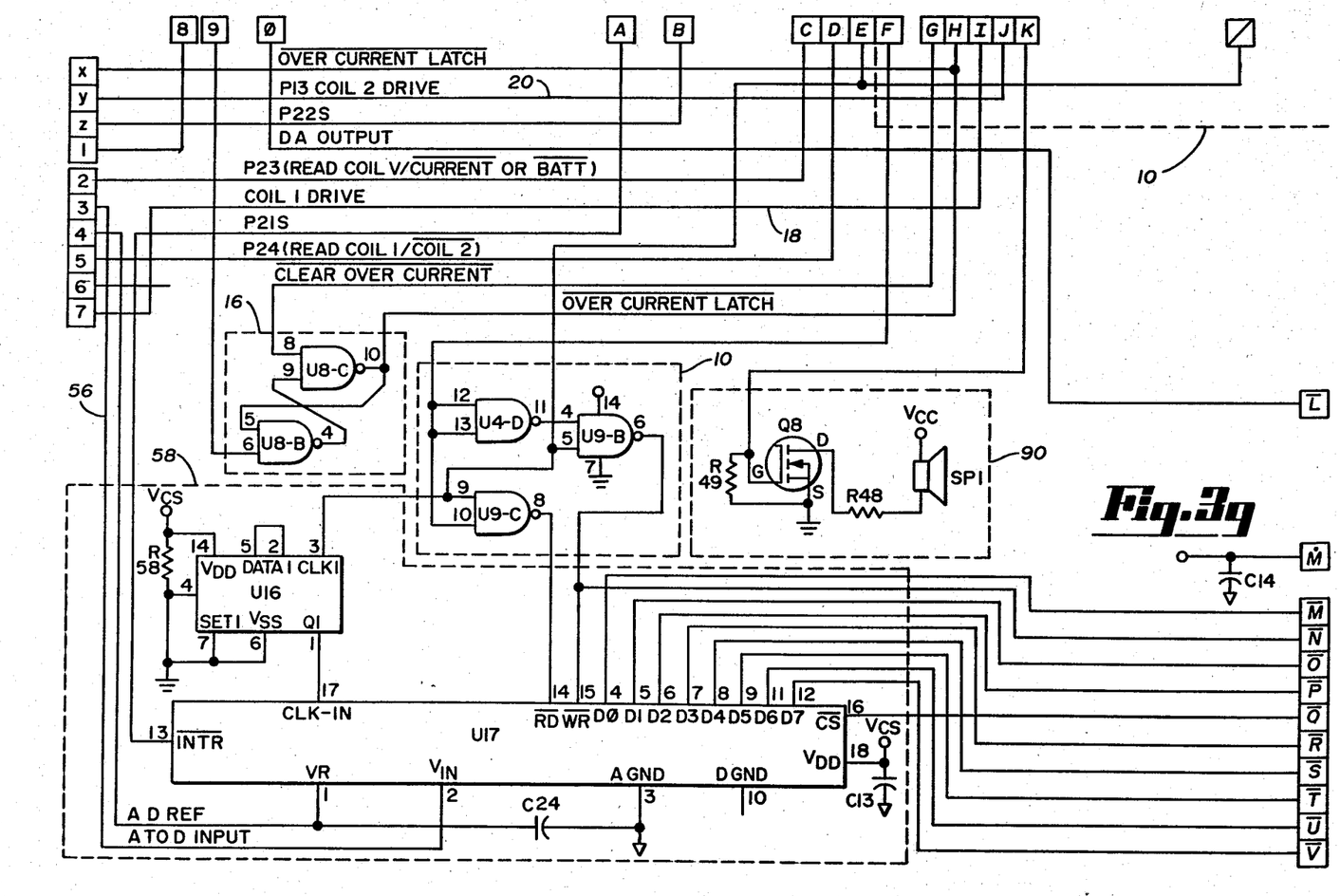
Figure 3H:
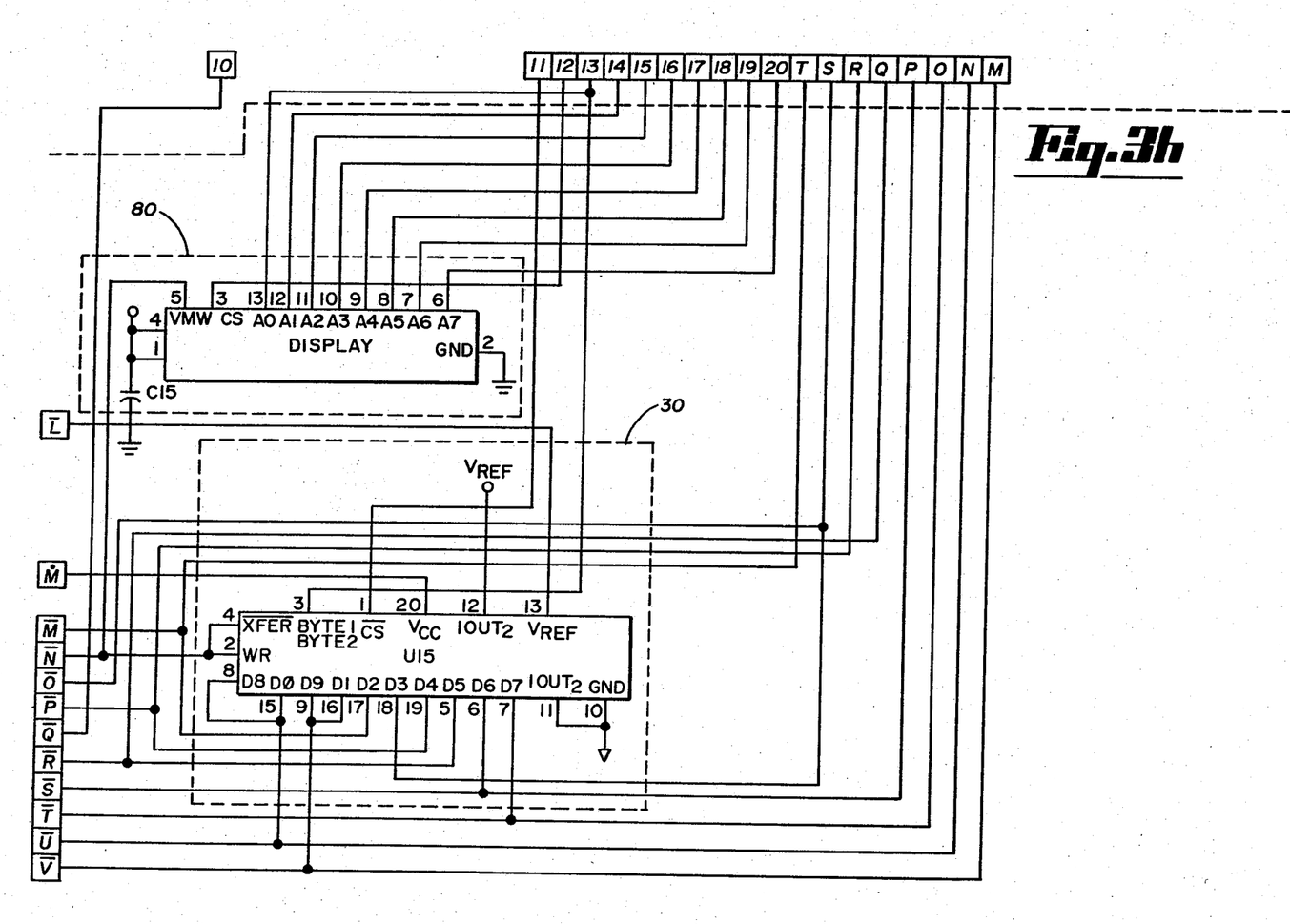
Figure 5F:
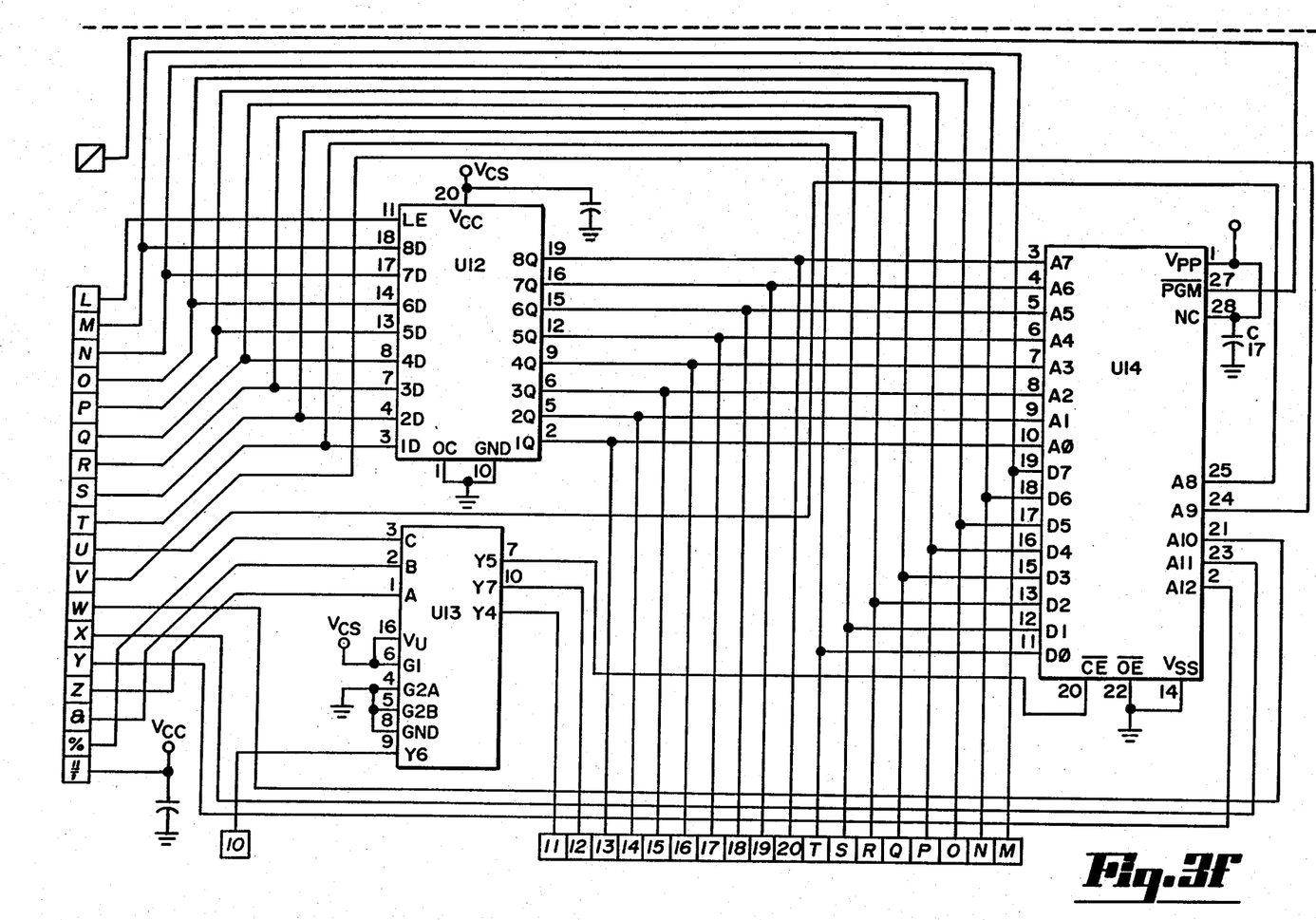

After a period of a few hundred microseconds, the conversion process will be complete and interrupt line pin 13 of converter U13 will pulse low indicating conversion is complete. At that time, microprocessor 11 reads results of the conversion by causing read pin 14 of converter U17 to pulse low along with select pin 16 of converter U17. The results of the conversion are then available on the data bus lines $D_0$-$D_7$.

Standby circuit and latch 68 (FIG. 3e) includes NAND gates U8A and U8B and transistors Q10 and Q11. Transistor Q10 is a P-channel junction FET. Transistor Q11 is an enhancement mode power FET. The latch includes the two NAND gates U8A and U8B connected together in a reset/set latch configuration, which functions in a manner similar to the overcurrent latch 16. The output of the latch goes to the gate of power FET Q11. The source of transistor Q11 is connected to ground. When the circuit is in a standby state, pin 3 of U8 will be high at a logic 1 which turns on transistor Q11, which in turn brings the drain very near to ground. This causes the reset input of microprocessor 11 pin 6 to be in a low state. At that time the microprocessor 11 is in the reset condition. At the same time STBY latch would be in a low state which forces the microprocessor to be in the standby mode. At this time power consumption of microprocessor 11 will be minimal. The internal clock is not running. The RAM memory stays alive.

The input at pin 12 of NAND gate U8D comes from diode CR15 and CR16 which are in turn connected to patient switch 64 and physician switch 66. When either switch is depressed, the cathodes of diodes CR15 or DR16 will be connected to ground, which in turn connects the common anodes of diodes CR15 and CR16 to one diode drop above ground. This in turn pulls pin 12, the standby latch clear input, to ground. When this input is brough to ground, the not-standby pin 11 goes to a high state and the standby latch is cleared. This action in turn starts the process of microprocessor 11 coming out of standby mode. The not-standby input (pin 7) to microprocessor 11 goes high.

Slightly later, the gate of transistor Q11 will go low at pin 3, the opposite side of the latch will be in the opposite state. The drain of transistor Q11 will then start going high as determined by an RC network of resistor 46 and capacitor C19. This will exponentially rise. Eventually this voltage causes the reset input of U11 to go to the high state, and microprocessor 11 starts running.

Transistor Q10 provides a secondary low voltage detect circuit to force the standby latch to be set into standby mode when voltage on the gate (which comes from $V_{DD}$) is below a threshold. When voltage $V_{DD}$ drops below the threshold gate voltage of transistor Q10, it will conduct. The drain is connected to ground thus pulling pin 2 of U8 to the low state which forces the standby latch into standby. During normal operation, the gate of transistor Q10 is at a relatively high level around 12 volts. In that case, pin 2 stays high unless forced low by another input. The other input comes through diode CR13 and through a multiplexer U10 ultimately from port 20 of microprocessor 11. Therefore, port 20 of microprocessor 11 has the ability to control or force the latch into standby as well. When port 20 pulses low, it causes pin 2 of gate U8A to pulse low. This puts the system in standby.

The set of resistors U18A comprises pull up resistors used in various places in the circuit. These resistors pull up patient switches and pull up a set of input conditions on chip U10. The function of multiplexer U10 is to initialize the microprocessor 11 in the proper state at the time of reset, but allow P20, P21, and P22 to be used elsewhere when not in reset.

Power switches 76 (FIG. 3a) include three different switches. All switches are P-channel power MOS FET transistors. Transistor Q5 controls the switched higher voltage of approximately 12 volts which is called $V_{DS}$. When the gate of transistor Q5 is brough to a low state, transistor Q5 turns on so that $V_{DS}$ will be at essentially the same voltage as the higher 12 volt supply $V_{DD}$. When the standby latch is set, the gate of Q5 is brough high and the transistor is turned off. Voltage is translated in the circuit by voltage controller U5 which serves as voltage translation from the 0-5 volt level of microprocessor 11 to the 0-12 volt level required for controlling the gate of transistor Q5.

The other two power switches are transistors Q6 and Q7 which control two switched 5 volt supplies. One is $V_{CS}$ from Q6 drain which is a 5 volt power use for the majority of the circuit. The other voltage comes from the drain of transistor Q7 and is the analog to digital reference voltage. This reference is also at 5 volts. The reference 5 v is isolated through a separate switch to minimize noise on the line. Transistors Q6 and Q7 are turned on when the gates are brought low via microprocessor 11 through standby latch control.

Another portion of voltage control that is comprised by coil driver circuitry 12 includes amplifier U4C and resistors R32, R33, and R34. This is a 9 volt supply. A capacitor C10 filters in order to minimize noise on the supply line. The three resistors R32 through R34 form part of the amplifier configuration of amplifier U4C. Resistors R33 and R32 provide feedback. Resistor R34 is an isolation resistor which prevents loading the output of a amplifier U4C with high capacitance which could cause instability in the amplifier.

Beeper 90 includes power FET transistor Q8 and a small electromagnetic transducer SP1. Transducer SP1 acts as a small speaker. Transistor Q8 is switched on and off at a rate determined by a drive signal emitted from port 14 of microprocessor 11. The drain of Q8 is connected through resistor R48 to transducer SP1. Resistor R48 is a current limiting resistor to control amount of drive power to the speaker. Resistor R49 is connected to pin 17 and to the source of transistor Q8, and then to ground. Resistor 49 acts as a pull down resistor so that when the system is in standby the beeper will be off and drawing no current.

PARTS LIST

| Resistors (K ohm) | | Resistors (K ohm) | |
|---|---|---|---|
| R1 | 51 | R30 | 200 |
| R2 | 10 | R31 | 24.9 |
| R3 | 10 (Pot) | R32 | 110 |
| R4 | 31.6 | R33 | 270 |
| R5 | 10 | R34 | 1 |
| R6 | 1 | R35 | 10 (Pot) |
| R7 | 100 | R36 | 20 |
| R8 | 1 | R37 | 4.7 |
| R9 | .01 ohm | R38 | 100 |
| R10 | 100 | R39 | 10 |
| R11 | 100 | R40 | 49.9 |
| R12 | 100 | R41 | 16.2 |
| R13 | 10 | R42 | 10 |
| R14 | 100 | R43 | 301 |
| R15 | 100 | R44 | 100 |
| R16 | 120 | R46 | 47 |
| R17 | 100 | R47 | 100 |
| R18 | 17.4 | R48 | 100 |
| R19 | 100 | R49 | 100 |
| R20 | 16.2 | R50 | 5.1 ohm |
| R21 | 100 | R51 | 100 |
| R22 | 49.9 | R52 | 49.9 |
| R23 | 100 | R53 | 10 |
| R24 | 50 (Pot) | R54 | 10 ohm |
| R25 | 63.4 | R55 | 100 |
| R26 | 28 | R56 | 100 |
| R27 | 100 | R57 | 10 |
| R28 | 200 | R58 | 10 |
| R29 | 100 | | |

| Capacitors (microfarads) | | Capacitors (microfarads) | |
|---|---|---|---|
| C1 | .1 | C13 | .1 |
| C2 | 6800 | C14 | .1 |
| C3 | .1 | C15 | .1 |
| C4 | .1 | C16 | .1 |
| C5 | 10 | C17 | .1 |
| C6 | .1 | C18 | .1 |
| C7 | .1 | C19 | 2.2 |
| C8 | .1 | C20 | 100 |
| C9 | 10 | C21 | .1 |
| C10 | 10 | C22 | 100 pf |
| C11 | 22 pf | C23 | 100 pf |
| C12 | 22 pf | C24 | .1 |
| | | C25 | .001 |

| Diodes | |
|---|---|
| CR1 | Axial lead 1 amp |
| CR2 | SES5301 |
| CR3 | Zener transient suppressor IN6288 |

-continued

PARTS LIST

| CR4 | SES5301 |
|---|---|
| CR5 | SES5301 |
| CR6 | Schottky IN5711 |
| CR7 | IN5354B |
| CR8 | Axial lead 1 amp |
| CR9 | Schottky IN5711 |
| CR10 | Schottky IN5711 |
| CR11 | Schottky IN5711 |
| CR12 | Schottky IN5711 |
| CR13 | Schottky IN5711 |
| CR14 | Schottky IN5711 |
| CR15 | Schottky IN5711 |
| CR16 | Schottky IN5711 |
| CR17 | Zener transient suppressor IN6288 |

| Transistors | |
|---|---|
| Q1 | P channel MOSFET |
| Q2 | Silicon switch |
| Q3 | IRF530 power FET |
| Q4 | IRF530 power FET |
| Q5 | ZVP01A34 |
| Q6 | ZVP01A34 |
| Q7 | ZVP01A34 |
| Q8 | VN0106N3 N channel MOSFET |
| Q9 | ZVN2110A |
| Q10 | J175 |
| Q11 | VN0106N3 |

| Miscellaneous Chips | |
|---|---|
| U1 | Quad op amp LM324 |
| U2 | C-CMOS 4050B |
| U3 | CMOS quad level shift 40109 |
| U4 | Quad op amp LM324 |
| U5 | CMOS quad level shift 40109 |
| U7 | LM2931T voltage regulator |
| U8 | CMOS Quad NAND CD 4011B |
| U9 | Quad NAND gate 74HC00 |
| U11 | Hitachi HD6303B |
| U12 | 74HC373 latch |
| U13 | HCMOS decoder 74HC138 |
| U14 | Hitachi or Ferranti 27C64, 8K × 8 EPROM |
| U15 | CMOS D to A converter 1008 |
| U16 | CD4013B |
| U17 | MSM5204 RS, OKI semiconductor |

SOFTWARE DESCRIPTION

As described above in the description of the circuit of the illustrated embodiment, microprocessor 10 controls operation of the system.

Self-Fitting

1. At the start of self-fitting, check to see if physician switch 66 is depressed for eight seconds. If so, go on.
2. Display message "SELF-FITTING" and begin self-fitting procedure.
3. Drive coils 7 and 8 for one second with 6 volts to allow settling.
4. Is the overcurrent latch set? If not, go on to step 6.
5. Display the message "CHECK COILS CHECK CABLES" and return to step 2.
6. Is battery voltage inadequate? If not inadequate, go on to step 9.
7. Initiate bad battery mode.
8. Go into standby mode and return to step 1.
9. Pulse coils for one second in burst pattern for settling.
10. Set up multiplexer 42 to read current.
11. Drive coils for one second to allow settling.
12. Put out a burst of 11 pulses with current read during pulse 1 and voltage read from alternating coils during the last 10 pulses. Save all values.
13. Is coil current too high? If not, go on to step 14. If too high, go to step 5.

14. Based on peak current is this a tibial coil? If so, go on to step 17.

15. Based on peak current is this a navicular coil? If not, go to step 5.

16. If a navicular coil, reset drive voltage to 10 volts and redo the 11 pulse sequence to get coil parameter values.

17. Is coil voltage within range? If so, go on to step 19.

18. If coil voltage out of range display "COILS TOO CLOSE" or "COILS TOO FAR" as appropriate and go to step 2.

19. Set digital to analog converter 58 using self-fitting look-up table values for specified coil type.

20. Pulse dummy burst for 2 seconds for output amplitude settling.

21. Emit bursts of 11 pulses reading current on first pulse and coil voltages on alternate coils for ten pulses.

22. Perform checks on new coil voltages. Read back and store average read back voltage and current for future reference during treatment.

23. Was an error detected after self-fitting?

24. If error, display "SELF-FIT ERROR" and go to 2.

25. If no error, display "SELF-FIT O.K." and go on.

26. Begin treatment.

The look up table is a table cross referencing drive voltage versus read back voltage. Read back values below a certain value on the table are considered to show that coils are too far apart. Values above a certain level on the table are believed to show that the coils are too close together. A particular set of tables are established for each type of coil used on the system.

The therapy pulses provided in this system are in bursts. During normal output pulse generation, pins P12 and P13 are pulsed simultaneously to drive output power FETS on and off. Pins P12 and P13 are pulsed high for 190 microseconds and low for 80 microseconds. Pulsing is continued for 21 pulses to complete the burst sequence. Burst patterns are repeated at the rate of 15 Hz. Pin P15 is pulsed as a logical "AND" of pins P12 and P13. That is, pin P15 is high whenever pins P12 and P13 are pulsed high.

Overcurrent Latch

Periodically, the condition of pin P11 is checked for an overcurrent mode. Pin P11 should normally be a "1" to indicate normal operation. When pin P11 is a "0", the output pulse generation is interrupted and the treatment timer is stopped. The overcurrent latch is reset by pulsing pin P10 low. Pin P10 is pulsed low and then brought high during a return from standby sequence and following an overcurrent condition during a non-pulsed time period. Pin P10 should be pulsed within 10 second of an overcurrent indication, but not less than 5 seconds following an overcurrent indication.

Current Measurement

When coil current is measured, pin 22 is set high and pin 23 is set low. Pin 24 can be in either state. During an output pulse sequence, a write is done to analog to digital converter 58 to start the sample and hold cycle 150 microseconds after the rising edge of the output pulse from pin P12 and P13. The analog to digital converter 58 is read after appropriate time to allow completion of conversion. The conversion factor in this embodiment is $FF_H$ (full scale) for current of 12 amperes.

Coil Voltage Measurement

To measure the voltage induced in a coil, the pulse drive to the coil is shut off and the opposite coil is driven. For measuring coil 7 voltage, pin P24 is set low and pins P22 and 23 are set high. Normal pulsing sequence is interrupted by pulsing only pin P13 high and keeping pin P12 low for one pulse at the first pulse of a burst sequence. Then analog to digital converter 58 is caused to sample and hold 90 microseconds after the leading edge of the pin P13 pulse to sample coil voltage approximately at the pulse midpoint. The analog to digital converter 58 is read after an appropriate delay. The conversion factor is FF (full scale) for a coil voltage of 1250 mV. To measure coil 8 voltage, pin 24 is set high and pin P22 and P23 are kept high. Pin P12 only is pulsed and the above procedure is repeated.

Analog To Digital Multiplexer

The multiplexer 42 controlled by pin P23 is switched at least 60 ms prior to making a coil voltage or current measurement to allow voltage at analog to digital conversion input to stabilize.

Current Check

At least once every 20 seconds, the microprocessor 11 measures the current in both coils pulsed at the V DRIVE voltage. Current is measured on the first pulse of a burst sequence only. This current is compared with a reference current for the coils (I COILS REF) previously measured. If the current measurements are not within 15 percent of each other, the message "CHECK COILS/CHECK CABLES" is displayed.

Field Strenght Check

Field strength checks are performed during burst sequences. Approximately once every 10 seconds (every 150 burst sequences) coil voltage is measured from each coil on the start of four consecutive burst sequences (a total of 4 readings). Two burst coil readings are compared with each other and two second coil readings are compared with each other. If the readings are not within 10 percent of each other the following message is displayed: "ELECTRICAL NOISE".

The two first coil readings are averaged and compared with the averages of the two second coil readings. If the two averages compare within 15 percent of each other, the treatment is continued. Otherwise the following message is displayed: "CHECK COILS/CHECK CABLES".

All four readings are averaged and compared with a reference average. If they are within 15 percent of each other, treatment is continued. Otherwise the following message is displayed: "COILS MISPLACED".

Total Elapsed Treatment Time

Whenever the unit is operating to provide a burst pattern output, an internal timer keeps track of total elapsed treatment time. The timer is stopped whenever an error condition occurs and it stops normal treatment output. This time is displayed when requested by the physician push button switch. The time is rounded to the nearest hour for total elapsed treatment time.

Treatment Time Per Session

Another timer keeps track of the treatment time per session to a resolution of 0.1 hour. This time is displayed as part of the message "___.___TREAT HOUR".

Number Of Treatment Sessions

A counter keeps track of the number of times the unit ran for at least ½ hour between a patient switch activation and a patient-activated off condition. Thus, a minimal treatment session is established as ½ hour. The number of treatment sessions is displayed by proper activation of the physician push button.

Physician Push Button

The physician push button switch 66 overrides the display 80 when it is displaying patient information. The single push button serves four functions: (1) request proper field strength, (2) request total time with therapy, (3) request total number of therapy sessions, and (4) reset therapy timer and counter and initialize self-fitting.

When physician switch 66 is first actuated, display 80 displays the message "MAG. STRENGTH O.K.", if the unit is currently operating properly and self-fitting has already occurred. If an error condition results, one of the following messages would be displayed just as if the system were in patient mode: "CHECK COILS/CHECK CABLES", "ELECTRICAL NOISE", "SELF-FIT ERROR", or "COILS MISPLACED".

A second activation of physician switch 66 causes the following message to be displayed: "\_\_\_\_\_TOTAL HOURS" with the number of treatment hours inserted.

The third activation of the physician switch 66 causes the following display: "\_\_\_\_TX. SESSIONS", with the number of sessions inserted.

The fourth activation causes the unit to revert to the same action as the first activation to start the sequence over again. If self-fitting has not occurred since the last power-up sequence, the physician switch, when depressed any number of times, causes display of the message "START FITTING".

Pushing and holding physician switch 66 at any time for more than eight seconds causes the treatment hours timer and number of treatment sessions to reset. It then initiates a self-fitting procedure and displays the message: "SELF-FITTING".

If the physician switch 66 has not been actuated for the last 60 seconds, display 80 automatically reverts to the normal display mode for patient information.

Normal Patient Information Display Mode

Display 80, when not being overridden by physician switch 66, displays the following message if the unit is operating properly: "\_\_\_.\_TREAT. HOUR". If the unit is not operating properly, one of the error messages will be displayed.

If the self-fitting procedure has not been correctly initiated since the last power-up sequence, the "NOT SELF-FITTED" message is displayed. The unit will not provide treatment output without self-fitting since the correct amplitude in not determined.

Patient On/Off Switch

The first actuation of patient switch 64 brings the unit out of standby mode. A second actuation causes standby mode when in patient mode. When the unit is powered up by a patient, the treatment time displayed starts from 0. If the patient switch 64 is pushed once while in physician mode, the unit goes to patient mode.

Battery Voltage

To read battery voltage, pin P22 is brought to 0. The state of P23 and P24 is irrelevant. The analog to digital converter 58 is read. The actual battery voltage is four times the reading. Battery voltage is periodically sampled at a time 1 to 30 milliseconds before the start of the burst sequence.

When this sample voltage reads from 11.9 volts to 11.6 volts, the following message is displayed: "CHARGE BATTERY". The unit keeps operating and the beeper is actuated once every minute.

When battery voltage reads from 11.6 volts to 10 volts, the following message is displayed: "CHARGE BATTERY". The system discontinues treatment and the beeper is actuated once every 10 seconds.

When battery voltage falls below 10 volts, the microprocessor is caused to go into standby mode. If 10 volts or less is measured on the first battery check after patient actuation, when coming out of standby mode, the following message is displayed: "CHARGE BATTERY". The beeper goes on and off for 15 seconds before the system goes back to standby mode.

Standby Mode

Following a patient-actuated off condition, microprocessor 10 pulses pin P20 low to cause the standby flip-flop to set. Pin P20 should normally be in the high state. Standby action removes the supply voltages from most of the circuitry to conserve power and extends battery life to hold the RAM contents. When a battery voltage of less than 10 volts is detected, the standby flip-flop will also be set. The standby flip-flop is cleared by activation of the patient switch 64 position switch 66.

Beeper

The audible beeper 80 is pulsed for approximately 1 second each 10 seconds during display of the message as described elsewhere in this section. The beeper is driven from pin P14 with 2500 to 3000 Hz pulses at approximately 50 percent duty cycle. Pin P14 will normally be placed in the low state when not actuating the beeper 90.

Error Condition Response

An error condition resulting in an error message of "CHECK COILS/CHECK CABLES", "SELF-FITTING", "ELECTRICAL NOISE" or "COILS MISPLACED" during normal patient operation mode results in termination of output pulses for 10 seconds followed by burst sequences during which the error condition is retested. If the error condition disappears, output pulses continue.

If any error condition (except low battery) continues during patient mode for more than 7 minutes, output pulses are terminated and the unit goes to standby.

Checksum Test

Each time the unit is placed in operation after return from standby, a checksum test will be performed on PROM memory. If this is normal, operation will continue as described. Otherwise the beeper will beep briefly and the unit will go to standby mode.

What is claimed is:

1. A medical device for inducing electrical current within a patient's body by creating a magnetic field through the body comprising:

first coil for placement in a treatment relation to a patient's body;

second coil for placement in a second treatment in relation to the patient's body so that the first coil and second coil are in a generally flux-aiding relation to each other;

driver circuitry for providing pulsed electrical energy to the first and second coils;

control means operably connected to the driver circuitry for controlling the magnitude of the electrical energy;

multiplexer means connected to the first coil and second coil and operably connected to the control means for selecting one coil; and the control means including means for indicating to the multiplexer means that one of the coils is selected for driving by the coil driver and the other of the coils is selected for sensing magnetic field induced by the other coil, and for automatically adjusting the magnitude of electrical energy produced by the driver circuitry based upon sensed magnetic field.

2. The device of claim 1 wherein the control means includes means for periodically sensing and for producing a warning signal if an improper field is sensed.

3. The device of claim 1 wherein the control means includes means for periodically sensing and for automatically adjusting during therapy.

4. A self-fitting electromagnetic bone growth stimulator comprising:

a first treatment coil for positioning adjacent a patient's body;

a second treatment coil for positioning adjacent a patient's body in a flux-aiding relationship which creates a magnetic field through a portion of the patient's body;

pulse generation means electrically connected to the first coil and the second coil for providing pulses of electrical energy to the first coil and the second coil;

control means electrically connected to the pulse generating circuitry for transmitting a magnitude signal to the pulse generation means indicative of a magnitude of the pulses of electrically energy;

sensing circuitry electrically connected to the first and second coils for sensing a magnetic field at one coil, which was produced by the other coil and for producing a sensed field signal indicative of field strength to the control means, the control means automatically adjusting the magnitude signal in response to the field strength signal.

5. The device of claim 4 wherein the control means includes means for periodically sensing and for producing a warning signal if an improper field is sensed.

6. The device of claim 4 wherein the control means includes means for periodically sensing and for automatically adjusting during therapy.

7. A device for automatically self-fitting an induction coil bone growth stimulator of the type having at least two coils for treating a patient comprising:

means for providing pulsed electrical energy to first and second coils;

means connected the first and second coils for selecting one coil as a sense coil;

control means operably connected to the means for providing pulsed electrical energy and the multiplexer means for indicating to the multiplexer means to select one coil for sensing, for sensing electrical current in the sense coil; and for automatically adjusting electrical energy provided by the means for providing pulsed electrical energy.

8. The device of claim 7 wherein the control means includes means for periodically sensing and producing a warning signal if an improper field is sensed.

9. The device of claim 7 wherein the control means includes means for periodically sensing and automatically adjusting during therapy.

* * * * *